United States Patent [19]

Masuda et al.

[11] Patent Number: 4,983,851
[45] Date of Patent: Jan. 8, 1991

[54] CONTACT THERAPEUTICAL APPARATUS

[75] Inventors: Isamu Masuda; Mitsuharu Hayashi, both of Fukuoka, Japan

[73] Assignee: Nihonkenkozoshinkenkyukai Co., Ltd., Fukuoka, Japan

[21] Appl. No.: 314,354

[22] PCT Filed: Apr. 13, 1988

[86] PCT No.: PCT/JP88/00367
§ 371 Date: Nov. 17, 1988
§ 102(e) Date: Nov. 17, 1988

[87] PCT Pub. No.: WO89/06991
PCT Pub. Date: Aug. 10, 1989

[30] Foreign Application Priority Data

Jan. 30, 1988 [JP] Japan .................. 63-11742
Feb. 23, 1988 [JP] Japan .................. 63-23634

[51] Int. Cl.$^5$ .................................. G21G 4/00
[52] U.S. Cl. ......................... 250/493.1; 128/399; 128/402
[58] Field of Search ............. 250/493.1; 219/354; 128/399, 402

[56] References Cited

U.S. PATENT DOCUMENTS

| | | | |
|---|---|---|---|
| 4,064,074 | 12/1977 | Ellis | 250/338.1 |
| 4,377,618 | 3/1983 | Ihada et al. | 219/354 |
| 4,602,238 | 7/1986 | Furtek | 219/354 |
| 4,620,086 | 10/1986 | Ades | 219/354 |
| 4,644,141 | 2/1987 | Hogen et al. | 250/493.1 |
| 4,680,822 | 7/1987 | Fujimo et al. | 128/399 |
| 4,850,340 | 7/1989 | Omishi | 128/24.1 |
| 4,886,972 | 12/1989 | Nakai et al. | 250/493.1 |

Primary Examiner—Bruce C. Anderson
Attorney, Agent, or Firm—Jordan and Hamburg

[57] ABSTRACT

A contact therapeutical apparatus for giving physical treatments such as magnetic and heat therapies by contacting the human body. The apparatus includes a heat generating portion inside a case body, and a far infrared radiating material is contained in the case body or a cover member covering the case body. The far infrared radiating material is exited by heat from the heat generating portion to radiate infrared rays and to heat inside the body sufficiently. There is provided a uniformalizing layer in the case body or cover member for distributing heat uniformly, and the far infrared radiating material is contained in the layer. Thereby, the uniform heating action by the infrared rays is obtained and the body can be warmed over in a wide area.

43 Claims, 7 Drawing Sheets

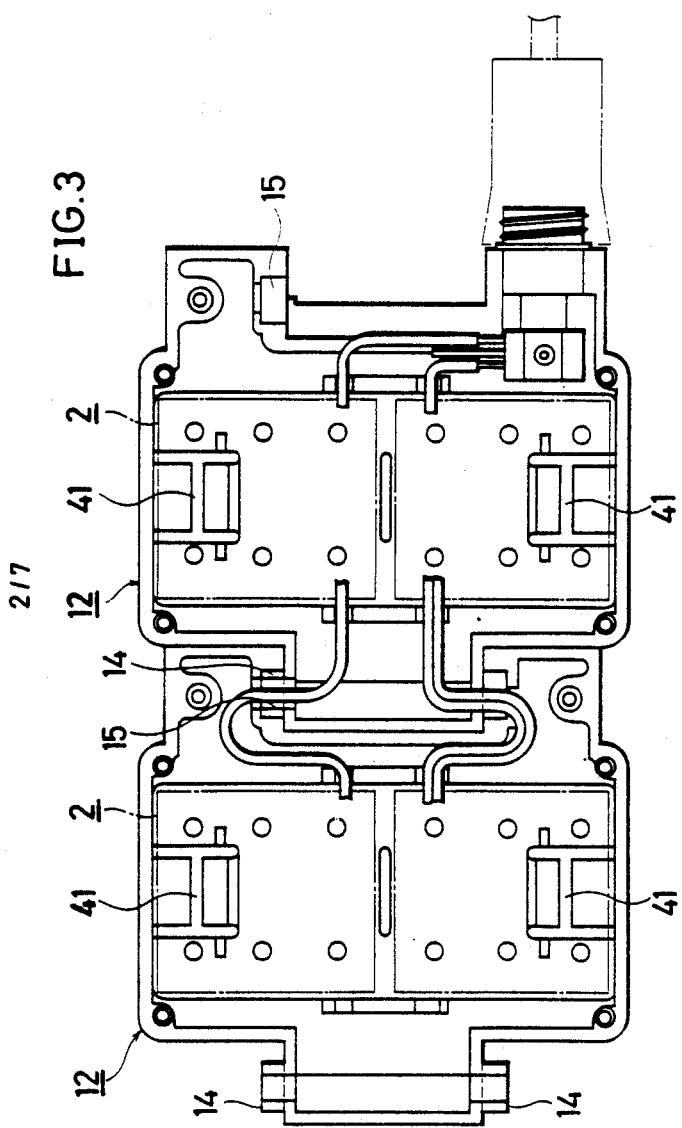

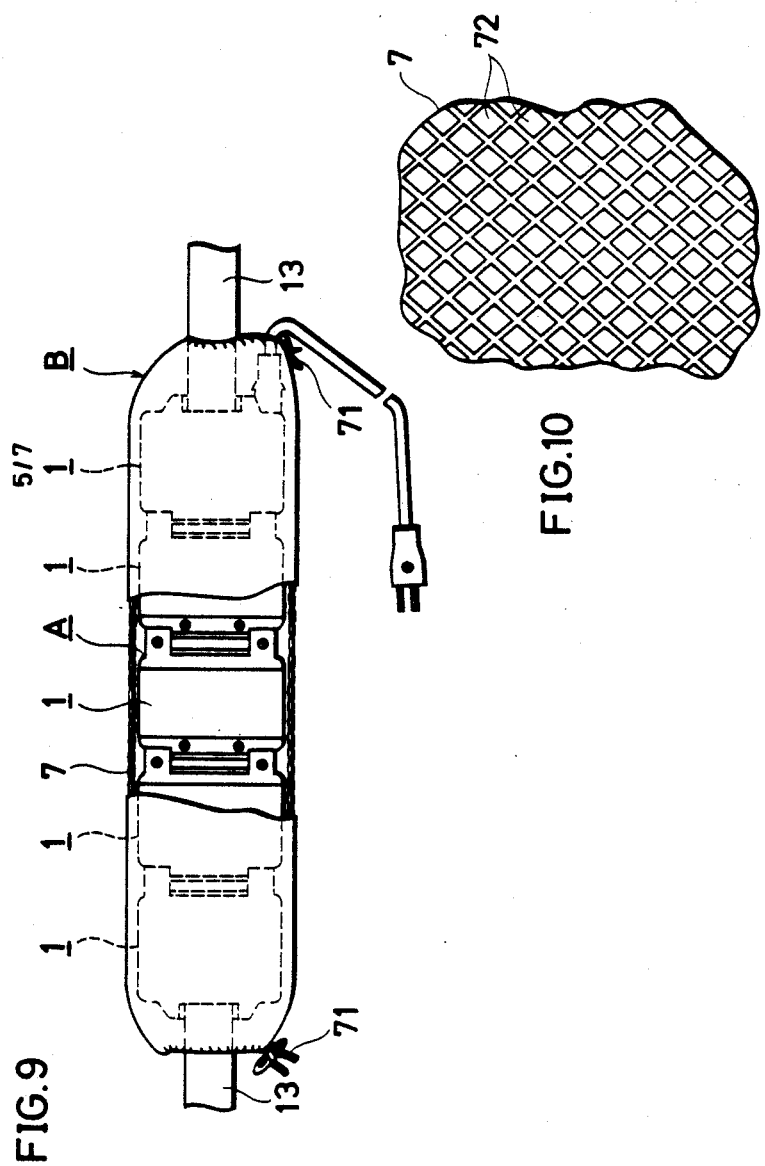

4,983,851

CONTACT THERAPEUTICAL APPARATUS

BACKGROUND OF THE INVENTION

1. Field of the Invention

The present invention relate to a contact therapeutical apparatus for giving physical treatments such as magnetic and heat therapies by contacting a human body.

2. Technical Background

I have, in the past, proposed a magnetic field generating therapeutical apparatus constructed by connecting a plurality of sealed cases containing a magnetic field generator consisting of an iron core wound with coils. The apparatus is so designed that when an AC current is applied to the coil, the magnetic field generator generates an alternating field which is applied to the body to improve various symptoms such as stiffness and so on. In the magnetic field generating therapeutical apparatus, the magnetic field generator generates vibration and heat when energized, thus in addition to the magnetic therapeutical effect, massaging and warming effects can be brought to a body.

In the case of aforesaid the apparatus, however, since heat generated in the magnetic field generator functions mainly on the surface of the body and lacking in warming the inside thereof, the warming effect is not sufficient.

The present invention has been devised in view of the problems aforementioned, and therefore, it is an object thereof to provide a novel contact therapeutical apparatus having a superb warming effect by providing on the case body a heat generating portion or a cover member covering the case body.

It is another object of the present invention to provide a novel contact therapeutical apparatus capable for warming the body uniformly to give the warming effect more effectively and provide a comfortable feeling.

DISCLOSURE OF THE INVENTION

The present invention relates to a contact therapeutical apparatus having a heat generating portion in a case body contacting the body, and containing a far infrared radiating material in the case body or the cover member covering the case body.

According to the present invention, when heat is generated in the heat generating portion, it is conducted to the case body or cover member, thereby the far infrared radiating material is excited to radiate far infrared rays. The far infrared rays radiated is applied to the body to warm inside the body to give effective warming effects. Since the far infrared radiating material is heated by the heat generated from the heat generating portion of the apparatus and radiates the far infrared rays, a special heat source is not required, resulting in simple production at low cost.

In the present invention, on the side of the case body contacting the body, for distributing heat uniformly, there is provided a uniformalizing layer, or inside the cover member covering the case body, the same uniformalizing layer is provided and at the same time, the far infrared radiating material is contained in the uniformalizing layer.

According to the present invention, heat is distributed uniformly to warm the body evenly in a wide area, thereby a more effective warming effect and comfortable feeling can be obtained.

BRIEF DESCRIPTION OF THE DRAWINGS

FIG. 3 is a plan view looking at a one half-body case from inside, FIG. 9 is a partly broken front view of a cover member covering a magnetic generating therapeutical apparatus, FIG. 10 is an enlarged view showing enlarged surface of materials constituting a cover member.

BEST MODE FOR CARRYING OUT THE INVENTION

Through the drawings show an example in which the present invention is embodied in a magnetic field generating therapeutical apparatus, it is not limited thereto, and it will be appreciated that the present invention may be applied in other various physical therapeutical apparatus as far as they include an internal heat generating portion.

Figure 1:
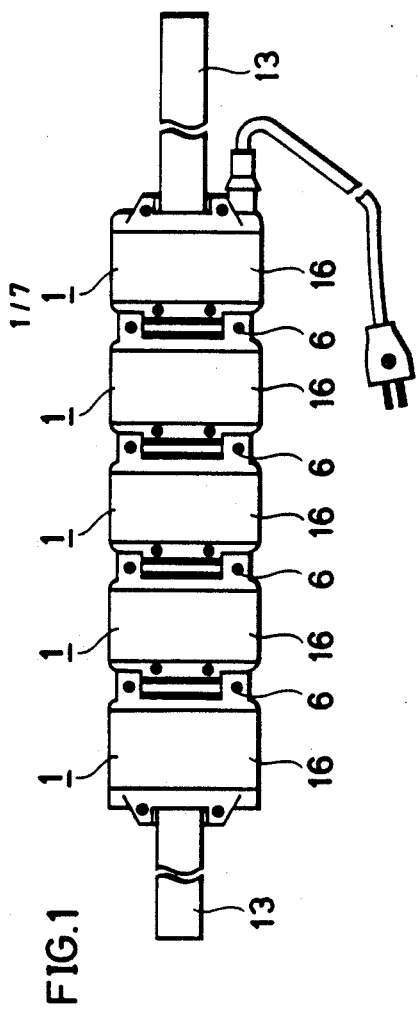
FIG. 1 is a front view of a magnetic field generating therapeutical apparatus according to one embodiment of the present invention.
Figure 2:
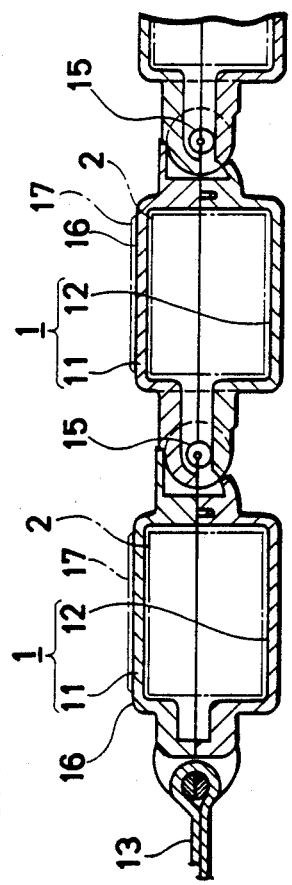
FIG. 2 is a horizontally cutaway sectional view of the embodiment shown in FIG. 1.

FIGS. 1 and 2 show the entire configuration of the magnetic field generating therapeutical apparatus according to one embodiment of the present invention, in which magnetic field generators 2 are disposed respectively in a plurality of plastic cases 1. Each case body 1 is pivotally connected in a row and on the case bodies 1, 1 positioned at opposite ends, and belts 13, 13 are mounted for interconnection.

The case body 1 is formed by a pair of half-body cases 11, 12 whose opening surfaces are brought face to face and secured by screws 6 at several locations. As shown in FIG. 2 and FIG. 3, on side end faces of the case body 1, either pivots 14, 14 or bearing holes 15, 15 are formed vertically to interconnect each case body 1, 1 pivotably by engaging the pivot 14 to the bearing hole 15 between the adjacent case bodies 1, 1.

Figure 4:
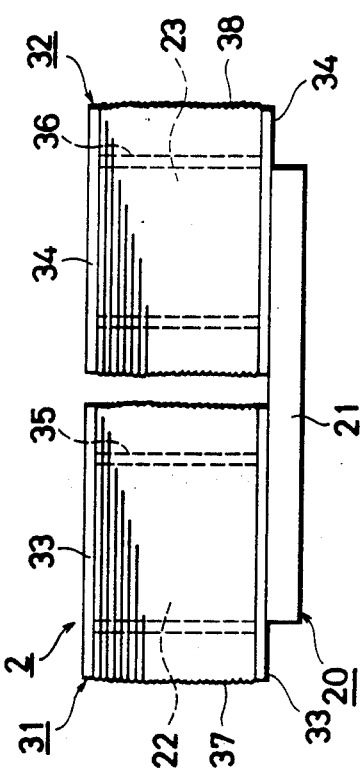
FIG. 4 is a front view showing the configuration of a magnetic field generator.

As shown in FIG. 4, the magnetic field generator 2 comprises a laminated iron core 20 including legs 22, 23 at opposite ends of a base 21, and coil bobbins 31, 32 engaged to respective legs 22, 23. The coil bobbins 31, 32 are constructed by winding coils 37, 38 around plastic spools 35, 36 having collars 33, 34 on opposite ends. When an AC current is applied to the coils 37, 38, an alternating field is generated from tips of the legs 22, 23.

As shown in FIG. 3, on the inner surface of one half-body case 12, positioning pieces 41, 41 for positioning the magnetic field generator 2 are projected integrally, thereby the base 21 of the laminated iron core 20 is positioned inside the two positioning pieces 41, 41.

The other half-body case 11 constitutes fixing means for the magnetic field generator 2 for forming a depression (not shown) on its inner surface for supporting the collars 33, 34 of the spools 35, 36, and the plate surface of the half-case body 11 constitutes a magnetic field active surface 16 which contacts to a human body.

On the magnetic field active surface 16 of the half-body case 11, a far infrared radiating material such as zirconia, zircon, titania, alumina, cozilite and silica is coated to form a radiation layer 17. Though the far infrared radiating material is excited by heat to radiate far infrared rays, besides coating the far infrared radiating material on the surface of the case body 1 as the present embodiment, this material may be mixed with forming materials of the case body 1.

Figure 5:
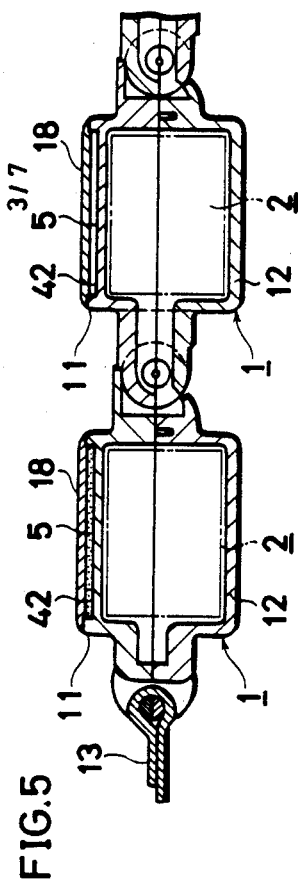
FIG. 5 is a horizontal sectional view showing another embodiment of the present invention.
Figure 6:
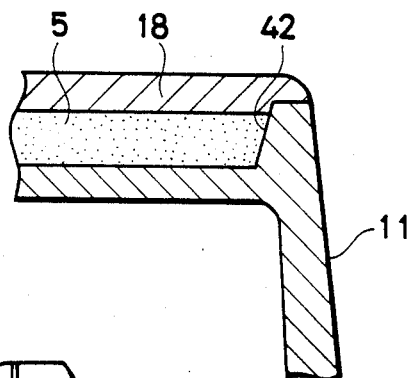
FIG. 6 is an enlarged sectional view of a case body showing the construction of a uniformalizing layer.

FIG. 5 shows another embodiment of the present invention, in which a uniformalizing layer 5 for distributing heat uniformly on the magnetic field active surface 16 of the half-body case 11 is formed. The uniformalizing layer 5 shown in the figure is, as shown in FIG. 6, formed by disposing a depression 42 throughout the entire magnetic field active surface 16 on the half-body case 11, filling a convection fluid such as air, water and oil or magnesium oxide having a good heat conductivity therein, and covering the opening with a transparent cover 18 by sticking or welding integrally.

Figure 7:
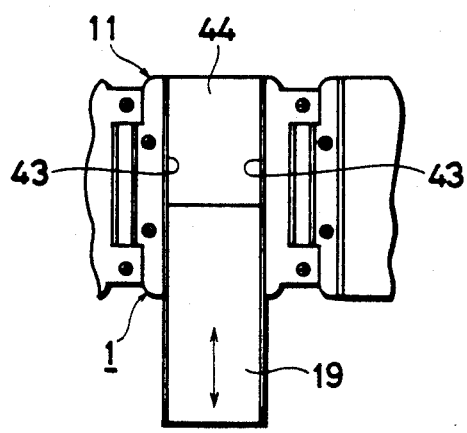
FIG. 7 is a plan view of a case body showing another forming process of a uniformalizing layer.
Figure 8:
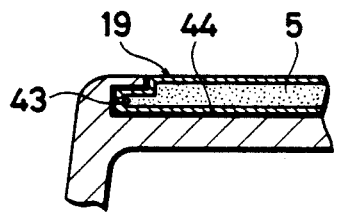
FIG. 8 is a sectional view showing part of the embodiment of FIG. 7.

FIGS. 7 and 8 show another forming process of the uniformalizing layer 5. In the figure, a mounting depression 44 having slide grooves 43, 43 on both sides thereof is formed on the magnetic field active surface 16 of the half-body case 11, and a mounting case 19 having the uniformalizing layer 5 therein is disposed removably with respect to the mounting depression 44. It is to be understood that the uniformalizing layer 5 is formed with air, water, oil, magnesium oxide and so on as same as aforementioned.

In the embodiment shown in FIGS. 5 to 8, although the far infrared radiating material may be mixed with the materials of case body 1 or coating it on the surface thereof, it is not limited thereto, in that the far infrared radiating material may be mixed in the uniformalizing layer 5.

FIG. 9 shows the entire configuration of the magnetic field generating therapeutical apparatus, in which a covering member B covers the apparatus A.

The apparatus A is constructed as same as those shown in FIGS. 1 to 4, wherein necessary corresponding parts are shown by like reference characters to omit its explanation.

The cover member B is constituted by a cylindrical bag having a length responsive to the connected length of a plurality of case bodies 1, 1. On both openings of the cover member B, there are provided fastening straps 71, 71 to cover the therapeutical apparatus A as if wrapping it in the bag. Though the cylindrical bag 7 is made of cloth such as woven or unwoven fabrics, it is not limited thereto, it may be formed with resin or rubber materials as far as they are soft and agreeable to the touch.

On the surface of cover member B, powdered materials containing the far infrared radiating material such as zirconia, zircon, titania, alumina, cozilite, silica, etc. are coated in a given pattern by printing as shown in FIG. 10 to form radiating portions 72 which are projected slightly. Though the far infrared radiating material is excited by heat to radiate infrared rays, besides printing on the cloth surface as the present embodiment, the cloth may be impregnated with the far infrared radiating material or woven by threads impregnated or coated with the far infrared radiating material.

Figure 11:
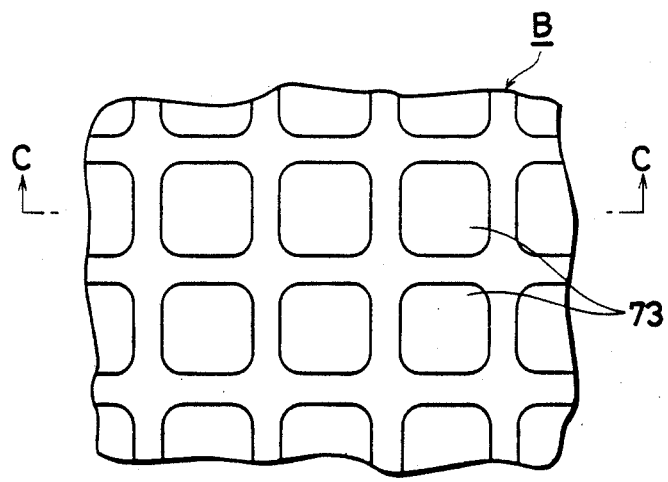
FIG. 11 is an enlarged view showing an enlarged surface of a cover member in which uniformalizing layers are formed.
Figure 12:
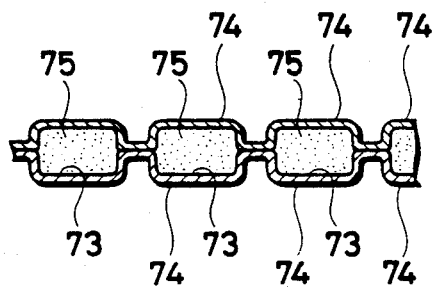
FIG. 12 is a sectional view taken along the line C—C of FIG. 11.

FIGS. 11 and 12 show another embodiment of the cover member B, wherein a uniformalizing layer 75 for distributing heat uniformly is formed. The uniformalizing layer 75 shown is constituted by overlapping two sheets of synthetic resin 74, 74 to construct the cover member B, forming a number of compartments 73, 73 between the sheets by means of thermal fusion or the like and filling a convection fluid such as air, water, oil, etc. or magnesium oxide having a good heat conductivity into each compartment 73.

In the aforesaid embodiment, though the entire therapeutical apparatus A is generally covered by the cover member B, it is not limited thereto, it may be covered partially.

Figure 13:
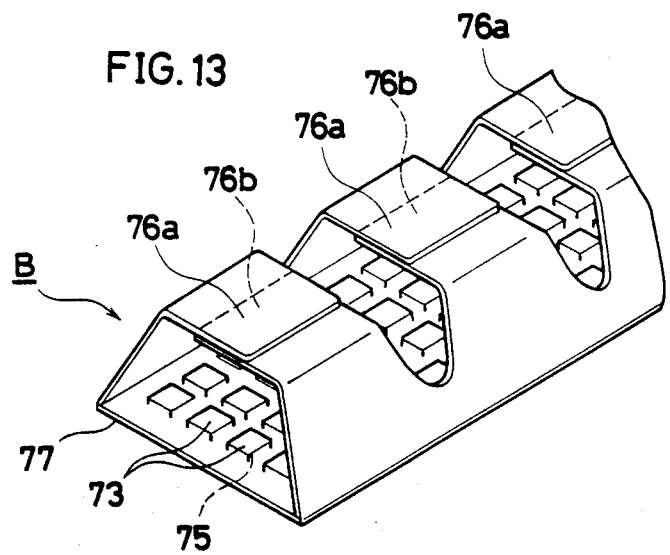
FIG. 13 is a perspective view showing another embodiment of a cover member.
Figure 14:
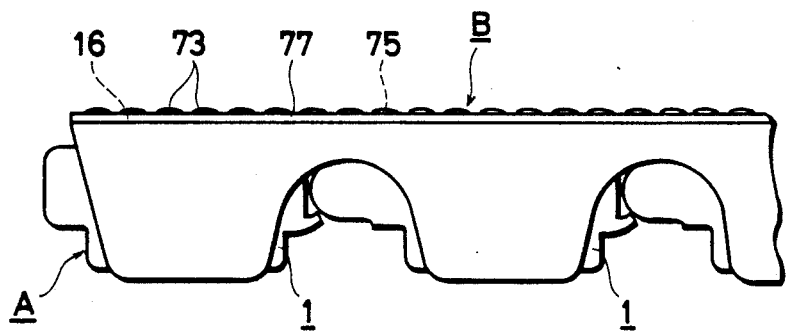
FIG. 14 is a plan view showing the state where a cover member of FIG. 13 is mounted on a therapeutical apparatus.

FIGS. 13 and 14 show the embodiment wherein the therapeutical apparatus A is covered partially and the uniformalizing layer 75 aforementioned is provided in the cover member B. The cover member B shown comprises a skin-contact portion 77 abutting the side of active surface 16 of the half-body case 11 in series, and mounting portions 76a, 76b which are connected at the rear of each case body 1, on overlapping surfaces of the mounting portions 76a, 76b, face fasteners (not shown) which engage and disengage one another are provided. In the skin-contact portion 77, as same as the embodiment of FIGS. 11 and 12, a number of compartments 73 are formed between the sheets, into which air, water, oil, magnesium oxide, etc. is filled to form the uniformalizing layer 75.

INDUSTRIAL APPLICABILITY

When using the magnetic field generating therapeutical apparatus, first, it is fastened about and fixed to a human body such that one or a plurality of case bodies 1 are contacted to portions of the body where stiffness or pain are generated or to the portion of fractured bone. Then, when a power is applied, coils 37, 38 of each magnetic field generator 2 are energized and their superposed magnetic fluxes are produced from the end faces of legs 22, 23 of the laminated iron core 20. Thereby, heat is generated at the iron core 20 and coils 37, 38, which is conducted to the case body 1 and cover member B. As a result, the case body 1 and cover member B are warmed and the far infrared radiating material is excited to radiate far infrared rays. The far infrared rays radiated acts on the body to warm therein and improves the warming effect.

When the uniformalizing layers 5, 57 are provided on the case body 1 and cover member B, they distribute the heat generated uniformly on the surfaces of the case body 1 and cover member B by the convection and heat conduction. Accordingly, heat is applied to the body evenly in a wide area to improve the warming effect and comfortable feeling.

What is claimed is:

1. A therapeutic apparatus to be disposed next to a person's body for effecting radiation of said person's body comprising: a casing means, heat-generating means within said casing means operable to generate heat, and far infrared radiating means disposed on said casing means, said far infrared radiating means being excited by the heat generated by said heat-generating means.

2. A therapeutic apparatus according to claim 1, wherein said radiating means comprises a coating disposed on at least a part of said casing means.

3. A therapeutic apparatus according to claim 1, wherein said casing means is made of a casing material, said radiating means comprising a far infrared radiating material mixed with said casing material.

4. A therapeutic apparatus according to claim 1, wherein said casing means comprises a uniformalizing material means for uniformly distributing heat which is generated by said heat-generating means.

5. A therapeutic apparatus according to claim 4, wherein said unit formalizing material means comprises a fluid.

6. A therapeutic apparatus according to claim 4, wherein said uniformalizing material means is selected from the group consisting of air, water and oil.

7. A therapeutic apparatus according to claim 4, wherein said uniformalizing material means comprises magnesium oxide.

8. A therapeutic apparatus according to claim 4, wherein said radiating means comprises a far infrared radiating material, said uniformalizing means comprising a uniformalizing material mixed with said radiating material.

9. A therapeutic apparatus according to claim 1, wherein said casing means has a casing portion which faces said person's body when in use, said casing means comprising a uniformalizing means on said casing portion for uniformly distributing heat.

10. A therapeutic apparatus according to claim 9, wherein said radiating means comprises radiating material mixed with said uniformalizing means.

11. A therapeutic apparatus according to claim 9, wherein said casing means has a depression at said casing portion, said casing means having a cover disposed over said depression to define a closed compartment between said depression and said cover, said uniformalizing means comprising a uniformalizing material within said compartment.

12. A therapeutic apparatus according to claim 11, wherein said radiating means comprises radiating material mixed with said uniformalizing material.

13. A therapeutic apparatus according to claim 11, wherein said cover is transparent.

14. A therapeutic apparatus according to claim 1 further comprising a uniformalizing material means on said casing means for uniformly distributing heat, said casing means comprising a cover means disposed over said uniformalizing material means.

15. A therapeutic apparatus according to claim 1 further comprising a uniformalizing means on said casing means for uniformly distributing heat said uniformalizing means comprising a uniformalizing material and a removeable support means for removeably supporting said uniformalizing material on said casing means.

16. A therapeutic apparatus according to claim 15, wherein said removeable support means comprises a slidable housing slidably mounted on said casing means, said housing containing said uniformalizing material.

17. A therapeutic apparatus according to claim 16, wherein said radiating means comprises a radiating material, said radiating material being disposed in said housing with said uniformalizing material.

18. A therapeutic apparatus according to claim 1 further comprising a uniformalizing means on said casing for uniformly distributing heat, said casing means comprising a casing housing, said uniformalizing means comprising a compartment means containing a uniformalizing material disposed in said compartment means, and detachable mounting means on said casing housing and on said compartment means for detachably mounting said compartment means on said casing housing.

19. A therapeutic apparatus according to claim 18 wherein said detachable mounting means comprises first slide means on said compartment means and second slide means on said casing housing, said first slide means being slidable on said second slide means to effect said detachable mounting of said compartment means on said casing housing.

20. A therapeutic apparatus according to claim 18, wherein said radiating means comprises a radiating material disposed in said compartment means with said uniformalizing material.

21. A therapeutic apparatus according to claim 1, wherein said radiating means comprises a cover means disposed over at least a part of said casing means, said radiating means further comprising a far infrared material carried by said cover means.

22. A therapeutic apparatus according to claim 21, wherein said cover means comprises a sleeve disposed about at least a part of said casing means.

23. A therapeutic apparatus according to claim 22, wherein said sleeve has longitudinal ends, and fastening means on said longitudinal ends for closing said longitudinal ends of said sleeve such that said sleeve thereby encloses at least a part of said casing means.

24. A therapeutic apparatus according to claim 21, wherein said cover means comprise a cloth material.

25. A therapeutic apparatus according to claim 21, wherein said cover means comprises a fabric material.

26. A therapeutic apparatus according to claim 21, wherein said cover means comprises a rubber material.

27. A therapeutic apparatus according to claim 21, wherein in said cover means comprises a resin material.

28. A therapeutic apparatus according to claim 21, wherein said far infrared radiating material is disposed on the surface of said cover means.

29. A therapeutic apparatus according to claim 21, wherein said cover means is impregnated with said far infrared radiating material.

30. A therapeutic apparatus according to claim 24, wherein said cover means comprises a fabric material made of threads, said threads being coated with said far infrared radiating material.

31. A therapeutic apparatus according to claim 21, wherein said cover means comprises a fabric material made of threads, said threads being impregnated with said far infrared radiating material.

32. A therapeutic apparatus according to claim 21, wherein said cover means further comprises uniformalizing material means for uniformly distributing heat.

33. A therapeutic apparatus according to claim 32, wherein said uniformalizing means comprises a uniformalizing material, said cover means having compartment means in which said uniformalizing material is disposed.

34. A therapeutic apparatus according to claim 33, wherein said compartment means comprises a plurality of spaced compartments.

35. A therapeutic apparatus according to claim 33, wherein said uniformalizing material means comprises a uniformalizing material disposed in said compartment means, said uniformalizing material comprising a fluid material.

36. A therapeutic apparatus according to claim 34, wherein said cover means comprises two sheets of synthetic resin joined to one another, each of said thermal sheets having compartment sections such that the compartment sections of one sheet are disposed in superimposed relationship with the compartment sections of another sheet to thereby define therebetween said plurality of spaced compartments.

37. A therapeutic apparatus according to claim 1, wherein said casing means has a casing portion which is juxtaposed to a person's body when in use, said far infrared radiating means comprising a cover means disposed at least partly about said casing means, and far infrared radiating material carried by said cover means.

38. A therapeutic apparatus according to claim 37, wherein said cover means has one section overlying said casing portion and another section which extends about said casing means.

39. A therapeutic apparatus according to claim 38, wherein said other section has two strap portions, and fastening means for fastening said two strap portions such that said cover means completely encircles said casing means.

40. A therapeutic apparatus according to claim 38, wherein said cover means comprises uniformalizing means at said one section for uniformly distributing heat.

41. A therapeutic apparatus according to claim 1, wherein said casing means comprises a plurality of casing units with each casing unit containing a heat-generating means, said casing means comprising pivot means for pivotably connecting said casing units.

42. A therapeutic apparatus according to claim 1, wherein said heat-generating means is operable to generate a magnetic field.

43. A therapeutic apparatus to be disposed next to a person's body for effecting radiation of said person's body comprising: a casing means, said casing means having a casing portion which faces said person's body, heat-generating means within said casing means operable to generate heat, uniformalizing means on said casing portion of said casing means for uniformly distributing heat which is generated by said heat-generating means, and far infrared radiating means on said casing means, said far infrared radiation means being excited by the heat generated by said heat-generating means, whereby said heat-generating means generates heat which is evenly distributed by said uniformalizing means and which excites said far infrared radiating means for effecting radiation of said person's body.

* * * * *